(12) United States Patent
Yang et al.

(10) Patent No.: US 10,940,113 B2
(45) Date of Patent: Mar. 9, 2021

(54) PHARMACEUTICAL COMPOSITION FOR COLON TARGETING, METHOD FOR TREATING A COLON-RELATED DISEASE USING THE SAME AND PREPARATION METHOD THEREOF

(71) Applicant: Medical And Pharmaceutical Industry Technology And Development Center, New Taipei (TW)

(72) Inventors: Chih-Chiang Yang, Taipei (TW); Wen-Che Wang, New Taipei (TW); Chiao-Ling Hsu, Taoyuan (TW)

(73) Assignee: MEDICAL AND PHARMACEUTICAL INDUSTRY TECHNOLOGY AND DEVELOPMENT CENTER, New Taipei (TW)

( * ) Notice: Subject to any disclaimer, the term of this patent is extended or adjusted under 35 U.S.C. 154(b) by 0 days.

(21) Appl. No.: 15/901,968

(22) Filed: Feb. 22, 2018

(65) Prior Publication Data

US 2018/0243220 A1 Aug. 30, 2018

Related U.S. Application Data

(60) Provisional application No. 62/462,955, filed on Feb. 24, 2017.

(30) Foreign Application Priority Data

Jan. 25, 2018 (TW) .................................. 107102685

(51) Int. Cl.
| | |
|---|---|
| A61K 9/20 | (2006.01) |
| A61K 9/28 | (2006.01) |
| A61K 31/196 | (2006.01) |
| A61K 31/606 | (2006.01) |

(52) U.S. Cl.
CPC ............ *A61K 9/205* (2013.01); *A61K 9/2846* (2013.01); *A61K 31/196* (2013.01); *A61K 31/606* (2013.01); *A61K 9/2893* (2013.01)

(58) Field of Classification Search
None
See application file for complete search history.

(56) References Cited

U.S. PATENT DOCUMENTS 5,681,581 A * 10/1997 Dunn .................... A61K 9/2077
424/468
5,840,332 A * 11/1998 Lerner ................... A61K 9/286
424/464

(Continued)

FOREIGN PATENT DOCUMENTS

EP 0809995 A1 * 12/1997 ........... A61K 9/1652

*Primary Examiner* — Aradhana Sasan
(74) *Attorney, Agent, or Firm* — Bacon & Thomas, PLLC (57) ABSTRACT

A pharmaceutical composition for colon targeting, a method for treating a colon-related disease using the same and a preparation method thereof are disclosed. The pharmaceutical composition of the present disclosure comprises: a core matrix comprising a cross-linked hydrogel and an active ingredient, wherein the active ingredient is dispersed in the cross-linked hydrogel, and a content of the active ingredient is 65 wt % to 95 wt % based on a total weight of the core matrix.

9 Claims, 6 Drawing Sheets

(56) References Cited

U.S. PATENT DOCUMENTS

| | | | |
|---|---|---|---|
| 2008/0317666 A1* | 12/2008 | Fattal | A61K 9/1652 424/1.11 |
| 2009/0028944 A1* | 1/2009 | Sathurappan | A61K 9/2009 424/482 |
| 2016/0008474 A1* | 1/2016 | Chang | A61K 9/5078 424/452 |

* cited by examiner

PHARMACEUTICAL COMPOSITION FOR COLON TARGETING, METHOD FOR TREATING A COLON-RELATED DISEASE USING THE SAME AND PREPARATION METHOD THEREOF

CROSS REFERENCE TO RELATED APPLICATION

This application claims the benefits of the Taiwan Patent Application Serial Number 107102685, filed on Jan. 25, 2018, the subject matter of which is incorporated herein by reference.

This application claims the benefit of filing date of U. S. Provisional Application Ser. No. 62/462,955, filed on Feb. 24, 2017 under 35 USC § 119(e)(1).

BACKGROUND

1. Field

The present disclosure relates to a pharmaceutical composition, a method for treating a colon-related disease using the same and a preparation method thereof and, more particularly, to a pharmaceutical composition for colon targeting, a method for treating a colon-related disease using the same and a preparation method thereof.

2. Description of Related Art

For most of the oral administered compositions for treating colon-related disease such as colitis or colon cancer, the active ingredients start to release before reaching colon. Hence, the amount of the active ingredients in the compositions has to be increased to ensure enough amounts of the active ingredients can reach colon. However, high dose of the active ingredients may cause side effects and the waste of the active ingredients.

Currently, the compositions for treating colon-related disease are formulated into layered particles. First, multi-layered drug particles are provided, wherein a core is sequentially coated with a drug layer and a coating film, and the multi-layered drug particles can successfully reach to colon. Next, the multi-layered drug particles and hydrogel particles (which can protect gastrointestinal tract and are prepared through a wet granulating process) are placed in a capsule, and the obtained capsule is coated with another coating film to protect the hydrogel particles. After the aforesaid process, the compositions for treating colon-related disease are prepared. However, the aforesaid process is very complicated, and two particles (i.e. the multi-layered drug particles and the hydrogel particles) have to be mixed. Hence, it is difficult to prepare the compositions for treating colon-related disease.

Therefore, it is desirable to provide a novel pharmaceutical composition, which can bring the active ingredient without early releasing. In addition, even though the novel pharmaceutical composition is formulated into single formulation, the effect achieved by using two mixed particles can still be accomplished.

SUMMARY

An object of the present disclosure is to provide a pharmaceutical composition for colon targeting, a method for treating a colon-related disease using the same and a preparing method thereof, wherein the pharmaceutical composition has high drug loading.

The pharmaceutical composition for colon targeting of the present disclosure comprises: a core matrix comprising: a cross-linked hydrogel and an active ingredient, wherein the active ingredient is dispersed in the cross-linked hydrogel, and a content of the active ingredient is 65 wt % to 95 wt % based on a total weight of the core matrix. In addition, the present disclosure further comprises a use of the aforesaid pharmaceutical composition for preparing a drug for treating a colon-related disease. Furthermore, the present disclosure also provides a method for treating a colon-related disease, which comprises administering the aforesaid pharmaceutical composition to a subject in need. Herein, examples of the colon-related disease may comprise colitis or colon cancer, but the present disclosure is not limited thereto.

Moreover, the present disclosure provides a method for preparing a pharmaceutical composition for colon targeting, which comprises the following steps: providing an active ingredient fluid, comprising a hydrogel and an active ingredient, wherein the active ingredient is dispersed in the hydrogel, a content of the hydrogel is ranged from 1 wt % to 4 wt % based on a total weight of the active ingredient fluid, and a content of the active ingredient is ranged from 10 wt % to 25 wt % based on the total weight of the active ingredient fluid; and adding the active ingredient fluid into a cross-linked solution dropwise to form a core matrix, wherein the core matrix comprises: a cross-linked hydrogel and the active ingredient, the active ingredient is dispersed in the cross-linked hydrogel, and a content of the active ingredient is 65 wt % to 95 wt % based on a total weight of the core matrix.

The conventional pharmaceutical composition is formed through a fluid bed granulation process, in which a core is coated with an active ingredient to form a core matrix. Hence, the conventional pharmaceutical composition has a core-shell structure formed with the core and the shell of the active ingredient. In the pharmaceutical composition, the active ingredient fluid is added dropwise into a cross-linked solution, and then the hydrogel is cross-linked to form a core matrix. Hence, the pharmaceutical composition of the present disclosure does not have the core-shell structure, and the active ingredient is dispersed in the cross-linked hydrogel. In addition, the drug loading of the conventional core matrix with the core-shell structure is less than 40%. In the pharmaceutical composition of the present disclosure, the core matrix is formed by dispersing the active ingredient into the cross-linked hydrogel, and the drug loading of the core matrix (i.e. the content of the active ingredient on the basis of the total weight of the core matrix) can be more than 40%, even be ranged from 65% to 95% because the hydrogel with high viscosity can bond with the active ingredient. Hence, when the pharmaceutical composition is prepared by the method of the present disclosure, the recycle rate of the active ingredient can be increased, and the increased recycle rate is much significant when the pharmaceutical composition is prepared in large scale.

In one embodiment of the present disclosure, an example of the core matrix can be a sphere. The size of the sphere is not particularly limited, and can be adjusted according to the product requirement.

In another embodiment of the present disclosure, the hydrogel or the cross-linked hydrogel may comprise alginate (for example, sodium alginate), chitosan, pectin or a combination thereof. When the hydrogel or the cross-linked hydrogel comprises alginate and pectin, a weight ratio between the alginate and the pectin is ranged from 1:1 to 1:0.5.

In another embodiment of the present disclosure, a content of the hydrogel can be ranged from 1 wt % to 4 wt % based on a total weight of the active ingredient fluid (1 wt %≤the content of the hydrogel 4 wt %). When the content of the hydrogel is less than 1 wt % or greater than 4 wt %, the viscosity of the active ingredient fluid may be too low or too high, resulting in the core matrix uneasily formed.

In another embodiment of the present disclosure, when the hydrogel used in the active ingredient fluid comprises alginate and pectin, a content of the pectin can be ranged from 0 wt % to 2 wt % based on the total weight of the active ingredient fluid (0 wt %=the content of the pectin ≤2 wt %). If the content of the pectin is greater than 2 wt %, the viscosity of the active ingredient fluid may be too high, resulting in the sphere core matrix uneasily formed.

In another embodiment of the present disclosure, a content of the active ingredient may be 65 wt % to 95 wt % (for example, 70 wt % to 950 wt % or 80 wt % to 90 wt %) based on a total weight of the core matrix.

In the method of the present disclosure, the cross-linked solution can be a calcium containing solution. Herein, a concentration of $Ca^{2+}$ in the cross-linked solution can be ranged from 0.15 to 0.4 mol/L. In one embodiment of the present disclosure, the calcium containing solution is a $CaCl_2$ solution, but the present disclosure is not limited thereto.

In the pharmaceutical composition of the present disclosure, the core matrix containing hydrogel can be dried for the following film coating process. Hence, the method of the present disclosure may further comprise a step of drying the core matrix after the step of forming the core matrix. Herein, the method for drying the core matrix is not particularly limited, and can be heat drying, freeze drying or other drying methods. If the heat drying is used, the drying temperature is not particularly limited and can be ranged from 30° C. to 100° C., for example, from 30° C. to 80° C., from 30° C. to 60° C. or from 40° C. to 50° C.

In one embodiment of the present disclosure, the method may further comprise a step of forming a coating film after the step of drying the core matrix, wherein the core matrix is coated with the coating film. Hence, the formed pharmaceutical composition may further comprise a coating film, wherein the core matrix is coated with the coating film. Herein, the coating film may comprise a pH dependent material, such as poly(methyl acrylate-co-methyl methacrylate-co-methacrylic acid), poly(methacrylic acid-co-ethyl acrylate) or a combination thereof. When the pharmaceutical composition is administered via oral administration, the core matrix without the coating film formed thereon may be degraded in the stomach. Hence, when the core matrix is further coated with the coating film, the degradation of the core matrix formed by the hydrogel in the gastrointestinal tract can be prevented. The pharmaceutical composition of the present disclosure can successfully passage the gastrointestinal tract because the coating film is formed with a pH dependent material. Meanwhile, when the pharmaceutical composition of the present disclosure reaches colon, the coating film is degraded because the pH of the colon environment is more than 6.0, and the active ingredient starts to release from the core matrix. Hence, the active ingredient carried by the hydrogel can successfully passage the gastrointestinal tract and release in the colon. In addition, in the pharmaceutical composition of the present disclosure, the hydrogel can be used as a carrier for the active ingredient. In addition, the degraded hydrogel can formed a protection layer on the colon wall to protect intestinal mucosa, and an effect of wound healing in the colon can also be achieved.

In one embodiment of the present disclosure, the active ingredient can be a medicine for treating colitis, such as mesalamine. However, the present disclosure is not limited thereto, and the active ingredient can be any water sparingly soluble to water insoluble ingredient to be carried to the colon, such as a vaccine, a probiotic, an antibody, a peptide, or other small molecule medicine.

In the present disclosure, the term "treating", "treat" or "treatment" refers to application or administration of the pharmaceutical composition to a subject with the purpose to cure, alleviate, relieve, alter, remedy, improve, or affect the disease, the symptom, or the predisposition. Herein, the aforesaid subject can be mammal, for example, human.

In addition, the pharmaceutical composition of the present disclosure may further selectively comprise at least one selected from the group consisting of: an active reactant, an adjuvant, a dispersant, a humectant, an excipient, and a suspension. Furthermore, the pharmaceutical composition can be applied via oral administration.

Other novel features of the disclosure will become more apparent from the following detailed description when taken in conjunction with the accompanying drawings.

DETAILED DESCRIPTION OF EMBODIMENT

The following embodiments when read with the accompanying drawings are made to clearly exhibit the above-mentioned and other technical contents, features and/or effects of the present disclosure. Through the exposition by means of the specific embodiments, people would further understand the technical means and effects the present disclosure adopts to achieve the above-indicated objectives. Moreover, as the contents disclosed herein should be readily understood and can be implemented by a person skilled in the art, all equivalent changes or modifications which do not depart from the concept of the present disclosure should be encompassed by the appended claims.

Experimental Process—Preparation of a Pharmaceutical Composition

First, hydrogel was dissolved in water, and solid components including an active ingredient were dissolved in the hydrogel solution to obtain an active ingredient fluid. Next, the active ingredient fluid was added dropwise into the cross-linked solution ($CaCl_2$ aqueous solution) After a predetermined cross-linking time, a drop pill (i.e. a sphere core matrix) was obtained. Then, the sphere core matrix was dried at 40° C. to 45° C., followed by a coating process to form a coating film on the sphere core matrix, After the aforesaid process, a pharmaceutical composition was obtained.

Embodiments 1-1 to 1-9 and Comparative Embodiments 1-1 to 1-2

In Embodiments 1-1 to 1-9 and Comparative embodiments 1-1 to 1-2, an encapsulator machine was used to prepare the sphere core matrix. Herein, the components and the conditions used in Embodiments 1-1 to 1-9 and Comparative embodiments 1-1 to 1-2 are listed in the following Table 1.

TABLE 1

Formulation of active ingredient fluid, cross-linking time, drug loading (LD) and entrapment efficiency (EE)

| | Sodium alginate (wt %) | CaCl$_2$ (mol/L) | Mesa- lamine (wt %) | Time (min) | LD (%) | EE (%) | LE + EE (%) |
|---|---|---|---|---|---|---|---|
| Embodiment 1-1 | 2 | 0.2 | 13 | 10 | 83.94 | 73.36 | 157.30 |
| Embodiment 1-2 | 2 | 0.3 | 16.67 | 30 | 82.63 | 77.31 | 159.94 |
| Embodiment 1-3 | 2 | 0.4 | 20 | 60 | 83.75 | 65.41 | 149.16 |
| Embodiment 1-4 | 3 | 0.2 | 16.67 | 60 | 79.76 | 65.51 | 145.27 |
| Embodiment 1-5 | 3 | 0.3 | 20 | 10 | 83.93 | 60.21 | 144.14 |
| Embodiment 1-6 | 3 | 0.4 | 13 | 30 | 73.61 | 64.34 | 137.95 |
| Embodiment 1-7 | 4 | 0.2 | 20 | 30 | 83.93 | 47.66 | 131.58 |
| Embodiment 1-8 | 4 | 0.3 | 13 | 60 | 65.78 | 51.15 | 116.93 |
| Embodiment 1-9 | 4 | 0.4 | 16.67 | 10 | 74.51 | 56.99 | 131.51 |
| Comparative Embodiment 1-1 | <1 | <0.1 | 20 | — | Drop pills were not formed. | | |
| Comparative Embodiment 1-2 | >4 | 0.2 | >25 | — | The viscosity of the acvie ingredient fluid was too high, and the active ingredient fluid cannot be dropped out. | | |

Drug loading=(drug content in a drug pill/total weight of the drug pill)×100%

Entrapment efficiency=(drug loading×total weight of the drug pills/total amount of the drug used)×100%

According to the results shown in Table 1, the core matrix obtained in Embodiments 1-1 to 1-9 has high drug loading. However, in Comparative embodiments 1-1 to 1-2, the core matrix cannot be obtained because the used amount of sodium alginate is too high or too low, the concentration of the CaCl$_2$ solution is too low, or the used amount of the active ingredient is too high (which means the used amount of the solid components is too high).

Embodiments 2-1 to 2-7 and Comparative Embodiments 2-1 to 2-2

In Embodiments 2-1 to 2-7 and Comparative embodiments 2-1 to 2-2, an encapsulator machine was used to prepare the sphere core matrix. Herein, the components and the conditions used in Embodiments 2-1 to 2-7 and Comparative embodiments 2-1 to 2-2 are listed in the following Table 2. In addition, the concentration of the CaCl$_2$ solution was fixed to be 0.2 mol/L, the cross-linking time was fixed to be 10 min, and the used amount of mesalamine was fixed to be 10 wt %.

TABLE 2

| | Sodium alginate (wt %) | Pectin (wt %) | Sodium alginate:Pectin | LD (%) | EE (%) |
|---|---|---|---|---|---|
| Embodiment 2-1 | 1 | 1 | 1:1 | 77.77 | 62.95 |
| Embodiment 2-2 | 1 | 2 | 1:2 | 71.06 | 67.76 |
| Embodiment 2-3 | 1.5 | 0.75 | 1:0.5 | 76.15 | 72.19 |
| Embodiment 2-4 | 1.5 | 1.5 | 1:1 | 72.33 | 67.75 |
| Embodiment 2-5 | 2 | 1 | 1:0.5 | 73.32 | 68.89 |
| Embodiment 2-6 | 2 | 2 | 1:1 | 65.98 | 54.17 |
| Embodiment 2-7 | 2.5 | 1.25 | 1:0.5 | 67.27 | 59.83 |
| Comparative Embodiment 2-1 | 1 | >2 | >1:2 | The viscosity of the acvie ingredient fluid was too high, and the active ingredient fluid cannot be dropped out. | |

Comparative embodiment 2-2: The used amount of the sodium alginate was less than 1 wt %. Drop pills were not formed no matter how much the pectin was used.

According to the results shown in Table 2, the core matrix obtained in Embodiments 2-1 to 2-7 has high drug loading. However, in Comparative embodiments 2-1 to 2-2, the core matrix cannot be successfully formed when the used amount of sodium alginate is too high or too low or the used amount of the pectin is too high.

Embodiments 3-1 and 3-2

In Embodiments 3-1 to 3-2, an encapsulator machine was used to prepare the sphere core matrix. After washing the sphere core matrix with de-ionized water, the clean sphere core matrix was put into 50° C. oven for drying 24 hr, and a semi-finished product was obtained. The final product was obtained by using the semi-finished product and a material for forming the coating film via a fluid bed granulation process, followed by adding 0.005% Talc and mixing well. Herein, the components and the conditions used in Embodiments 3-1 to 3-2 are listed in the following Table 3. In addition, the cross-linking time was fixed to be 10 min.

TABLE 3

| Formulation | | Embodiment 3-1 | Embodiment 3-2 |
|---|---|---|---|
| Active ingredient fluid | Sodium alginate (wt %) | 3 | 2 |
| | Pectin (wt %) | — | 1 |
| | Mesalamine (wt %) | 16.67 | 10 |
| | Water (wt %) | 80.33 | 87 |
| Cross-linked solution | $CaCl_2$ (mol/L) | 0.2 | 0.5 |
| Coating film | Core matrix (g) | 400 | 300 |
| | Eudragit FS30D (g) | 40.5 | 30.4 |
| | Tween 20 (g) | 4 | 3 |
| | Water (g) | 184.5 | 138.4 |
| Yield | — | 98.88% | 98.67% |
| LD of the semi-finished product (%) | — | 83.04 ± 0.28 | 74.96 ± 0.37 |
| LD of the final product (%) | — | 75.98 ± 0.24 | 68.77 ± 0.26 |

The pharmaceutical compositions prepared in Embodiments 3-1 and 3-2 were analyzed through a dissolution analysis. At 0-2 hr, the pharmaceutical compositions were put in 0.1 N HCl solution; at 2-6 hr, the pharmaceutical compositions were put in pH 6.0 solution; and at 6-14 hr, the pharmaceutical compositions were put in pH 7.5 solution. Meanwhile, the dissolved percentages were measured every hour. The results are shown in FIG. 1.

Figure 1:
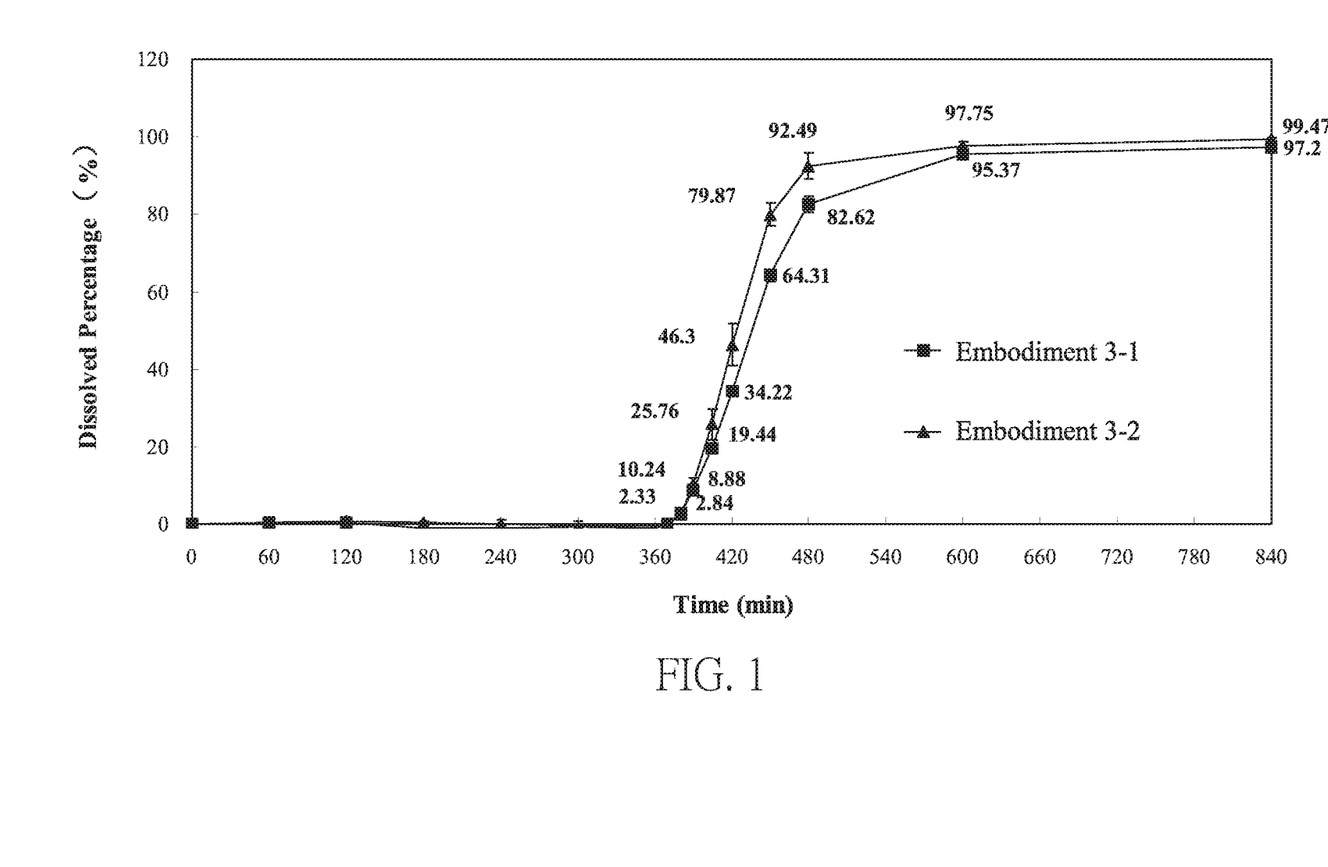
FIG. 1 is a graph showing dissolution profiles of pharmaceutical compositions prepared in Embodiments 3-1 and 3-2.

As shown in FIG. 1, the pharmaceutical compositions prepared in Embodiments 3-1 and 3-2 did not release the active ingredient in 0.1 N HCl solution and pH 6.0 solution, but started to release the active ingredient in pH 7.5 solution. These results indicate that the pharmaceutical compositions prepared in Embodiments 3-1 and 3-2 can successfully start to release the active ingredient after reaching the colon.

Embodiments 3-3 to 3-6

The pharmaceutical compositions of Embodiments 3-3 and 3-4 are similar to those of Embodiments 3-1 and 3-2, except for the materials of the coating films. The coating film made of poly(methyl acrylate-co-methyl methacrylate-co-methacrylic acid) can be dissolved above pH 7.0, and the coating film made of poly(methacrylic acid-co-ethyl acrylate) can be dissolved above pH 5.5. In the pharmaceutical compositions of Embodiments 3-1 and 3-2, the coating films were made of poly(methyl acrylate-co-methyl methacrylate-co-methacrylic acid), and the used amount of poly(methyl acrylate-co-methyl methacrylate-co-methacrylic acid) was 10 wt % based on the weight of the sphere core matrix. In the pharmaceutical compositions of Embodiments 3-3 and 3-4, the coating films were made of poly(methacrylic acid-co-ethyl acrylate), and the used amount of poly(methacrylic acid-co-ethyl acrylate) was 20 wt % based on the weight of the sphere core matrix.

The pharmaceutical compositions of Embodiments 3-5 and 3-6 are similar to those of Embodiments 3-3 and 3-4, except that the used amount of poly(methacrylic acid-co-ethyl acrylate) was increased to 40 wt % in the pharmaceutical compositions of Embodiments 3-5 and 3-6.

The drug loadings of the semi-finished products and the final products of Embodiments 3-3 to 3-6 are listed in the following Table 4.

TABLE 4

| | Embodiment 3-3 | Embodiment 3-4 |
|---|---|---|
| LD of the semi-finished product (%) | 83.78 ± 0.75 | 74.94 ± 0.09 |
| LD of the final product (%) | 64.85 ± 0.36 | 56.73 ± 0.62 |

TABLE 4-continued

| | Embodiment 3-5 | Embodiment 3-6 |
|---|---|---|
| LD of the semi-finished product (%) | 83.78 ± 0.75 | 74.94 ± 0.09 |
| LD of the final product (%) | 55.86 ± 0.44 | 40.05 ± 0.05 |

The pharmaceutical compositions prepared in Embodiments 3-3 to 3-6 were analyzed through a dissolution analysis. At 0-4 hr, the pharmaceutical compositions were put in 0.1 N HCl solution; and at 4-12 hr, the pharmaceutical compositions were put in pH 6.0 solution. Meanwhile, the dissolved percentages were measured every hour. The results are shown in FIG. 2 and FIG. 3.

Figure 2:
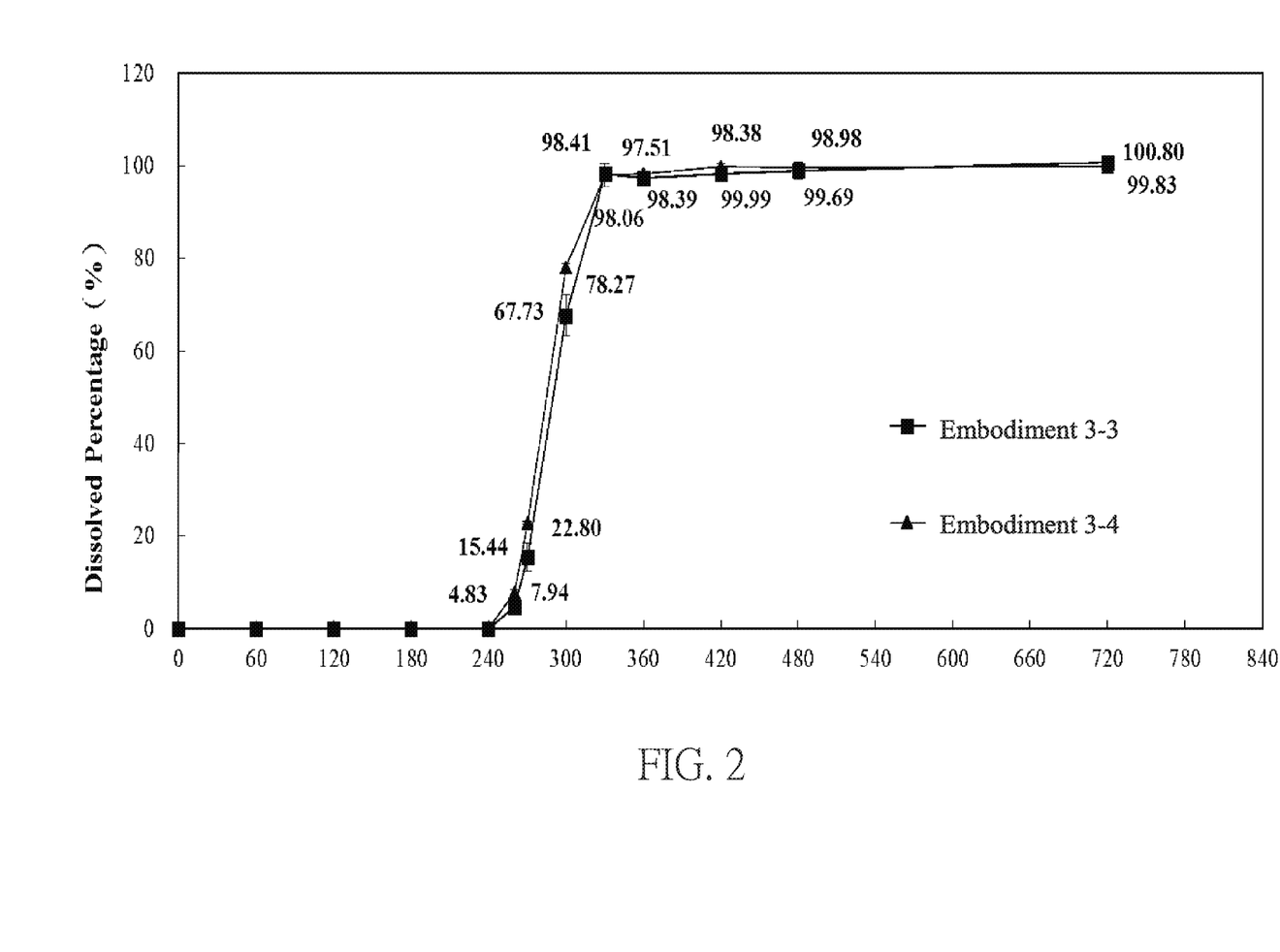
FIG. 2 is a graph showing dissolution profiles of pharmaceutical compositions prepared in Embodiments 3-3 and 3-4.
Figure 3:
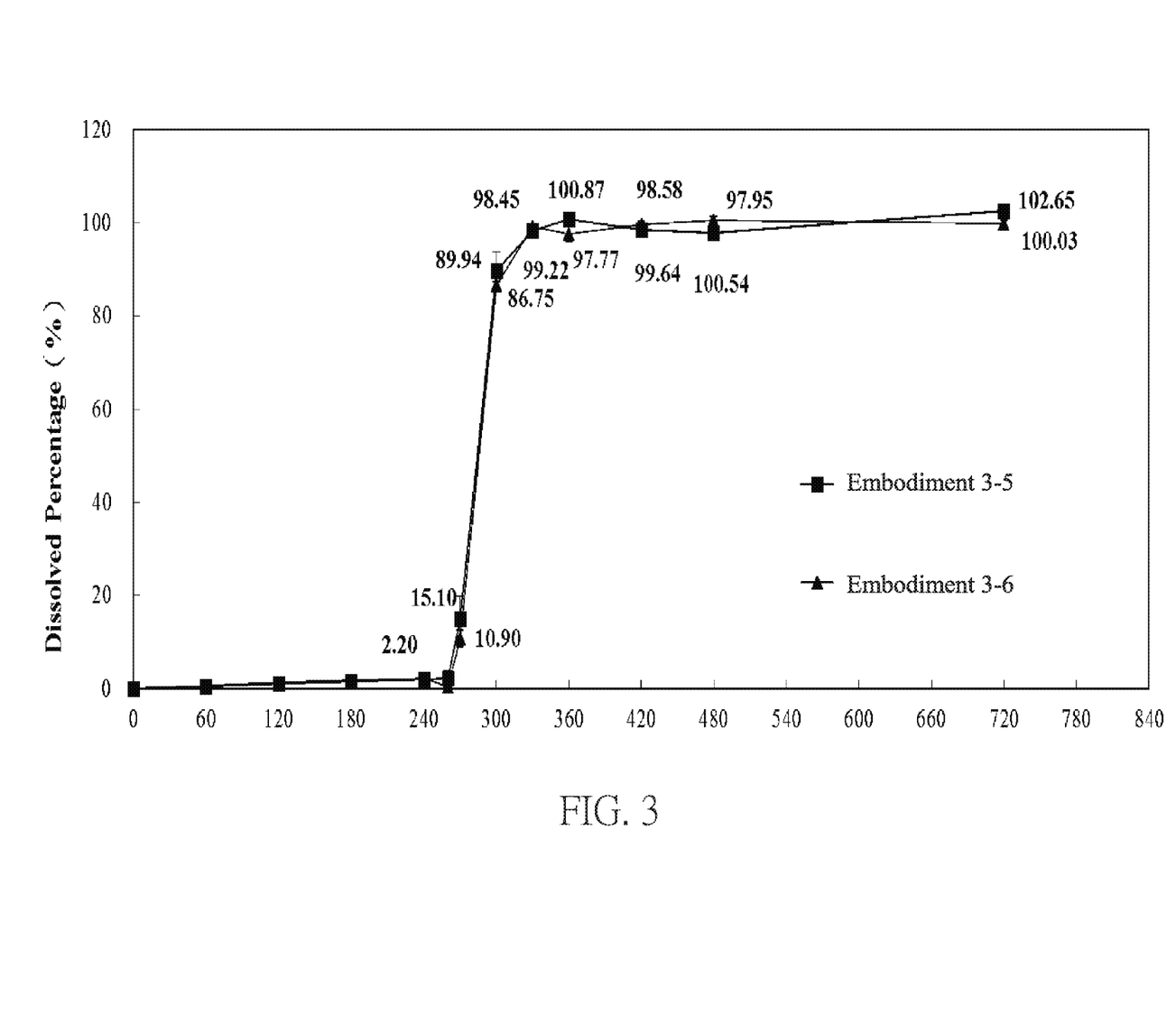
FIG. 3 is a graph showing dissolution profiles of pharmaceutical compositions prepared in Embodiments 3-5 and 3-6.

As shown in FIG. 2 and FIG. 3, the pharmaceutical compositions prepared in Embodiments 3-3 to 3-9 did not release the active ingredient in 0.1 N HCl solution, but started to release the active ingredient in pH 6.0 solution. These results indicate that the pharmaceutical compositions prepared in Embodiments 3-3 to 3-6 can successfully start to release the active ingredient after reaching the targeting environment (for example, colon Experimental Process—Animal Test Male Wistar mice were starved for 24 hr, and distal colitis was induced via intracolonic injection of DNBS (2,4-dinitrobenzene sulfonic acid, 30 mg in 0.5 mL ethanol (30%)). Then, 2 mL air was injected after instillation of the enema to ensure the solution was remained in the colon. The test substance (the pharmaceutical composition of Embodiment 3-1) and mesalamine were oral administered 24 hr and 2 hr prior to the DNBS injection, followed by administering one dose a day, and 5 days. The total doses of the test substance and mesalamine were 7 doses. The body weight, fecal occult blood and fecal consistency were recorded every day during the experiment. The animals were sacrificed at Day 8. The adhesions of colon and other organs were observed after abdominal opening, the colitis still can be observed, and the colon was carried out and weighted.

After dissection, the exist of the pharmaceutical composition sphere can be observed in the gastrointestinal tract before colon, but no pharmaceutical composition sphere is found in the colon. This result indicates that pharmaceutical composition of the present disclosure can pass the first half part of the gastrointestinal tract and is degraded in colon.

In addition, the evaluation indicators for inflammation and colon width as well as the total score are listed in the following Table 5.

TABLE 5

| | Dose | Adhesion | Strictures | Ulcers/Inflammation | Colon width | Total score |
|---|---|---|---|---|---|---|
| Sham control (without DNBS) | N/A | 0.0 ± 0.0 | 0.0 ± 0.0 | 0.0 ± 0.0 | 0.0 ± 0.0 | 0.0 ± 0.0 |
| Vehicle control | 2.5 mL/ animal qd × 7, PO | 0.0 ± 0.0 | 2.8 ± 0.2 | 3.8 ± 0.6 | 1.0 ± 0.0 | 7.6 ± 0.7 |
| Embodiment 3-1 | 2 CAP/ animal qd × 7, PO | 0.0 ± 0.0 | 2.0 ± 0.0 | 3.2 ± 0.62 | 1.0 ± 0.0 | 6.2 ± 0.2 |
| Mesalamine | 2 CAP/ animal qd × 7, PO | 0.0 ± 0.0 | 2.6 ± 0.2 | 3.2 ± 0.54 | 1.0 ± 0.0 | 6.8 ± 0.76 |

Figure 5:
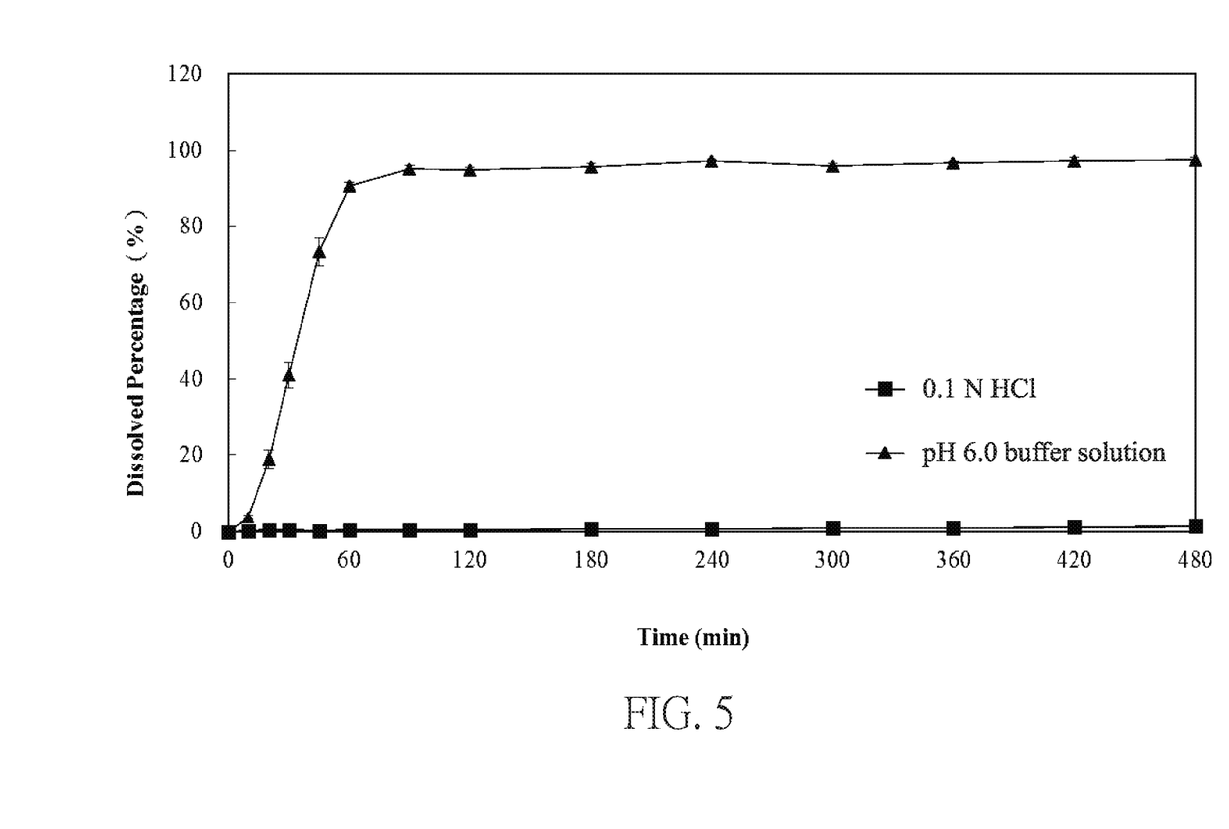
FIG. 5 is a graph showing a dissolution profile of pharmaceutical composition prepared in Embodiment 4-2.

As shown in FIG. 5, the pharmaceutical compositions of the present disclosure show better effect on inflammation and colon width as well as the total score, and these results indicates that the pharmaceutical composition of the present disclosure has colon targeting effect.

Embodiment 4-1—Large Scale Process

In Embodiment 4-1, an encapsulator machine was used to prepare the sphere core matrix in large scale. The components and the conditions used herein are listed in the following Table 6. In addition, the cross-linking time was fixed to be 10 min.

TABLE 6

Formulation of the core matrix and the process conditions

|  | Formulation | Weight (g) | Concentration |
|---|---|---|---|
| Active ingredient fluid | Sodium alginate | 30 | 1.5 wt % |
|  | Pectin | 15 | 0.75 wt % |
|  | Mesalamine | 440 | 22 wt % |
|  | Water | 1515 | 75.75 wt % |
| Cross-linked solution | CaCl$_2$ | 111.1 | 0.2 mol/L |
|  | Water | 4888.9 | — |
| Core speed |  | 8 rpm |  |
| Vibrating motor speed |  | 100 rpm |  |
| Blowing control |  | 0.1 bar |  |

TABLE 7

Formulation of the coating filim and the process conditions

|  | Formulation | Weight (g) | Solid (g) |
|---|---|---|---|
| Coating film | Core matrix | 430 |  |
|  | Eudragit FS30D | 145.12 | 43.54 |
|  | Tween 20 | 21.50 | 4.3 |
|  | Water | 79.55 |  |
| Coating time | 2 hr | Yield (%) | 98.67 |
| Inlet temperature (Set) | 34-36° C. | Outlet temperature | 28-30° C. |
| Product temperature (On process) | 30-31° C. | Spry rate (g/min) | 3.5-4.8 |
| Spray pressure (act) | 1.5 | Vilocity of air | 35% |

Embodiment 4-2

The pharmaceutical compositions of Embodiment 4-2 is similar to that of Embodiment 4-1, except that the active ingredient fluid does not contain pectin, and the concentration of the sodium alginate was increased to 2 wt %. In addition, in Embodiment 4-2, poly(methyl acrylate-co-methyl methacrylate-co-methacrylic acid) used in Embodiment 4-1 was substituted with poly(methacrylic acid-co-ethyl acrylate). In both Embodiments 4-1 and 4-2, the used amounts of poly(methyl acrylate-co-methyl methacrylate-co-methacrylic acid) and poly(methacrylic acid-co-ethyl acrylate) were respectively 10 wt % based on the weight of the core matrix.

The drug loadings of the semi-finished products and the final products of Embodiments 4-1 and 4-2 are listed in the following Table 8.

TABLE 8

|  | Embodiment 4-1 | Embodiment 4-2 |
|---|---|---|
| LD of the semi-finished product (%) | 88.77 ± 0.23 | 91.23 ± 0.40 |
| LD of the final product (%) | 80.74 ± 0.17 | 81.42 ± 0.50 |

The pharmaceutical compositions prepared in Embodiments 4-1 and 4-2 were analyzed through a dissolution analysis. The results are shown in FIG. 4 and FIG. 5.

Figure 4:
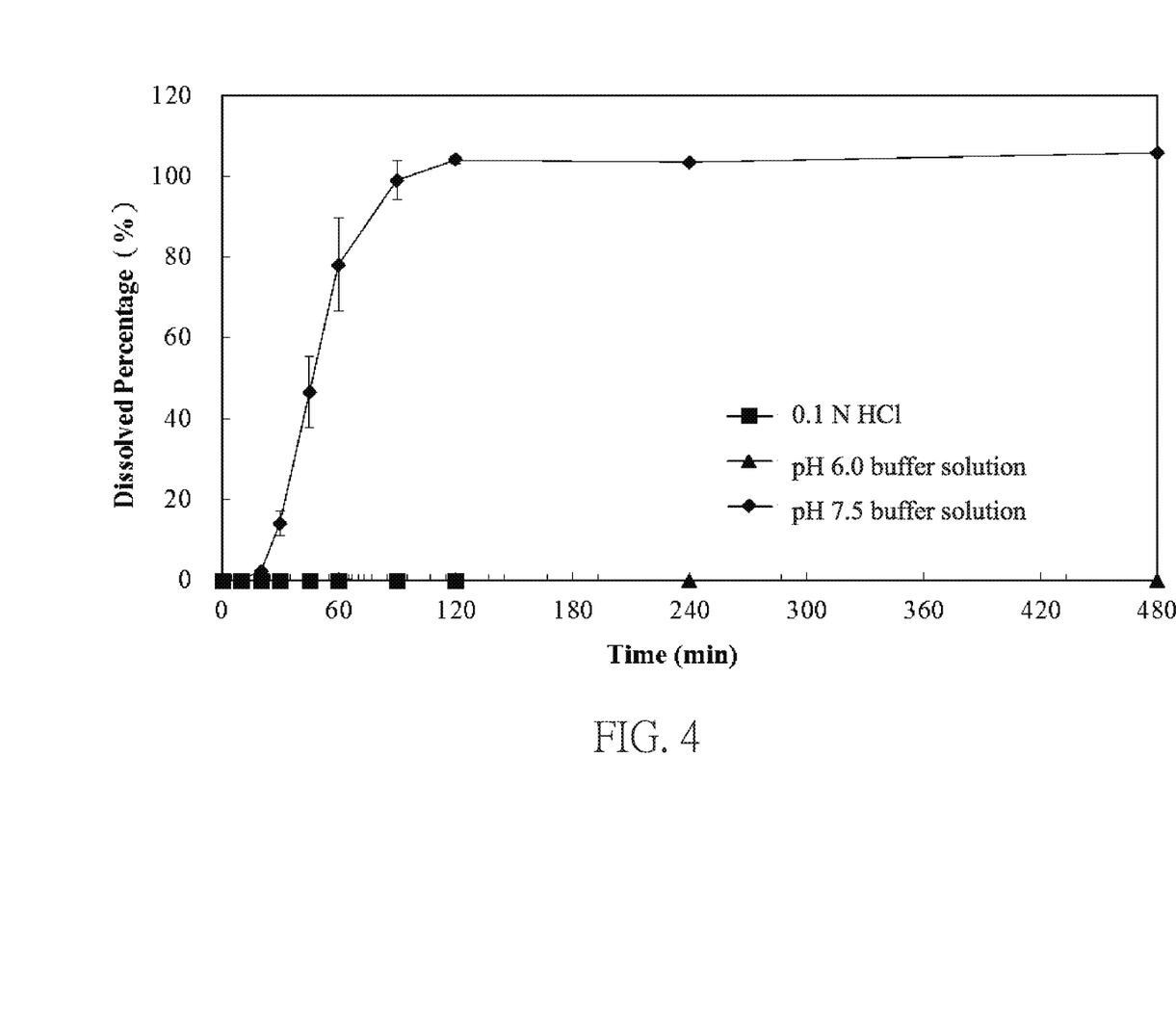
FIG. 4 is a graph showing a dissolution profile of pharmaceutical composition prepared in Embodiment 4-1.

As shown in FIG. 4 and FIG. 5, the pharmaceutical compositions prepared in Embodiments 4-1 and 4-2 did not release the active ingredient in 0.1 N HCl solution. The pharmaceutical composition prepared in.

Embodiment 4-1 started to release in pH 7.5 solution, and the pharmaceutical composition prepared in Embodiment 4-2 started to release in pH 6.0 solution. These results indicate that the pharmaceutical compositions prepared in Embodiments 4-1 and 4-2 can successfully start to release the active ingredient after reaching the targeting environment (for example, colon).

Figure 6:
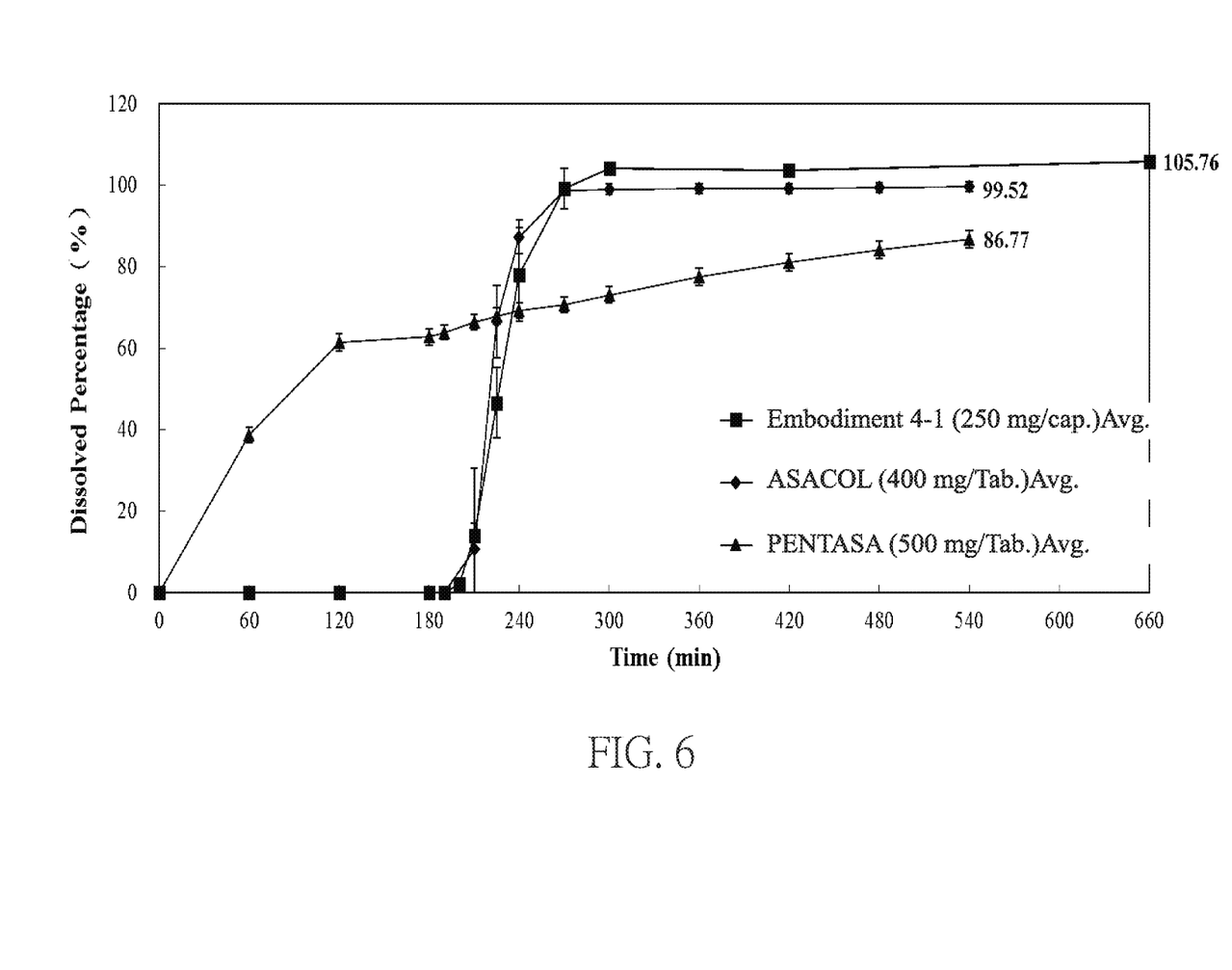
FIG. 6 is a graph showing dissolution profiles of 400 mg/Tab Mesalamine, 500 mg/Tab Mesalamine and a pharmaceutical composition prepared in Embodiment 4-1.

In addition, 400 mg/Tab Mesalamine, 500 mg/Tab Mesalamine and the pharmaceutical composition prepared in Embodiment 4-1 were analyzed through a dissolution analysis. At 0-2 hr, the pharmaceutical composition of Embodiment 4-1 was put in 0.1 N HCl solution; at 2-3 hr, the pharmaceutical composition was put in pH 6.0 solution; and at 3-11 hr, the pharmaceutical composition was put in pH 7.5 solution. At 0-2 hr, 400 mg/Tab Mesalamine was put in 0.1 N HCl solution; at 2-3 hr, 400 mg/Tab Mesalamine was put in pH 6.0 solution; and at 3-9 hr, 400 mg/Tab Mesalamine was put in pH 7.5 solution. At 0-2 hr, 500 mg/Tab Mesalamine was put in 0.1 N HCl solution; at 2-3 hr, 500 mg/Tab Mesalamine was put in pH 6.0 solution; and at 3-9 hr, 500 mg/Tab Mesalamine was put in pH 7.2 solution.

As shown in FIG. 6, the pharmaceutical composition of Embodiment 4-1 and 400 mg/Tab Mesalamine started to release the active ingredient in pH 7.5 solution, which indicates the pharmaceutical composition of Embodiment 4-1 can successfully start to release the active ingredient after reaching the targeting environment (for example, colon).

The results shown in the aforesaid embodiments indicate that the pharmaceutical composition prepared by the method of the present disclosure can successfully start to release the active ingredient after reaching the targeting environment (for example, colon) and the purpose of colon targeting can be achieved.

Although the present disclosure has been explained in relation to its embodiment, it is to be understood that many other possible modifications and variations can be made without departing from the spirit and scope of the disclosure as hereinafter claimed.

What is claimed is:

1. A method for treating a colon-related disease, comprising:
    administering a pharmaceutical composition to a subject in need,
    wherein the pharmaceutical composition comprises:
    a core matrix comprising: a cross-linked hydrogel and an active ingredient, wherein the active ingredient is mesalamine and dispersed in the cross-linked hydrogel, and a content of the active ingredient is 65 wt % to 95 wt % based on a total weight of the core matrix,
    wherein the core matrix is coated with a coating film comprising a pH dependent material.

2. The method of claim 1, wherein the cross-linked hydrogel comprises alginate, chitosan, pectin or a combination thereof.

3. The method of claim 2, wherein the cross-linked hydrogel comprises alginate and pectin, and a weight ratio between the alginate and the pectin is ranged from 1:1 to 1:0.5.

4. The method of claim 1, wherein the coating film comprises poly(methyl acrylate-co-methyl methacrylate-co-methacrylic acid), poly(methacrylic acid-co-ethyl acrylate) or a combination thereof.

5. The method of claim 1, wherein the pharmaceutical composition is administered via oral administration.

6. A pharmaceutical composition for colon targeting, comprising:
- a core matrix comprising: a cross-linked hydrogel and an active ingredient,
- wherein the active ingredient is mesalamine and dispersed in the cross-linked hydrogel, and a content of the active ingredient is 65 wt % to 95 wt % based on a total weight of the core matrix, and
- wherein the core matrix is coated with a coating film comprising a pH dependent material.

7. A method for preparing a pharmaceutical composition for colon targeting, consisting essentially of the following steps:
- providing an active ingredient fluid, comprising a hydrogel and an active ingredient, wherein the active ingredient is mesalamine and dispersed in the hydrogel, a content of the hydrogel is ranged from 1 wt % to 4 wt % based on a total weight of the active ingredient fluid, and a content of the active ingredient is ranged from 10 wt % to 25 wt % based on the total weight of the active ingredient fluid; wherein the hydrogel comprises alginate and pectin, and a weight ratio between the alginate and the pectin is ranged from 1:1 to 1:0.5;
- adding the active ingredient fluid into a calcium containing solution dropwise to form a core matrix, wherein a concentration of $Ca^{2+}$ in the calcium containing solution is ranged from 0.15 mol/L to 0.4 mol/L and the core matrix comprises: a cross-linked hydrogel and the active ingredient, the active ingredient is dispersed in the cross-linked hydrogel, and a content of the active ingredient is 65 wt % to 95 wt % based on a total weight of the core matrix;
- drying the core matrix; and
- forming a coating film, after the step of drying the core matrix, wherein the core matrix is coated with the coating film comprising a pH dependent material.

8. The method of claim 7, wherein the calcium containing solution is a CaCl2 solution.

9. The method of claim 7, wherein the coating film comprises poly(methyl acrylate-co-methyl methacrylate-co-methacrylic acid), poly(methacrylic acid-co-ethyl acrylate) or a combination thereof.

* * * * *